United States Patent [19]
Edmund et al.

[11] Patent Number: 6,114,283
[45] Date of Patent: Sep. 5, 2000

[54] HERBICIDAL MIXTURES

[75] Inventors: Richard Manly Edmund; Otis Wilson Howe, III, both of Little Rock, Ark.

[73] Assignee: E. I. du Pont de Nemours and Company, Wilmington, Del.

[21] Appl. No.: 09/338,290

[22] Filed: Jun. 22, 1999

Related U.S. Application Data

[60] Provisional application No. 60/094,359, Jul. 28, 1998.

[51] Int. Cl.[7] ................................................ A01N 43/54
[52] U.S. Cl. ............................................................ 504/136
[58] Field of Search ...................... 504/116, 136

[56] References Cited

U.S. PATENT DOCUMENTS

| | | | |
|---|---|---|---|
| 4,420,325 | 12/1983 | Sauers | 71/92 |
| 4,668,277 | 5/1987 | Yamamoto et al. | 71/92 |
| 4,746,353 | 5/1988 | Levitt | 71/90 |
| 4,931,081 | 6/1990 | Wolf | 71/92 |
| 4,954,164 | 9/1990 | Suzuki et al. | 71/92 |
| 4,994,571 | 2/1991 | Miki et al. | 544/331 |
| 5,009,699 | 4/1991 | Brady et al. | 71/92 |
| 5,017,212 | 5/1991 | Ishida et al. | 71/92 |
| 5,104,443 | 4/1992 | Kehne et al. | 71/92 |

FOREIGN PATENT DOCUMENTS

| | | | |
|---|---|---|---|
| WO 93/00011 | 1/1993 | WIPO | A01N 47/36 |
| 9321772 | 11/1993 | WIPO . | |
| WO 93/21772 | 11/1993 | WIPO | A01N 47/36 |
| 9707678 | 3/1997 | WIPO . | |
| 9710710 | 3/1997 | WIPO . | |
| WO 97/08151 | 3/1997 | WIPO | C07D 239/54 |
| WO 97/27753 | 8/1997 | WIPO | A01N 47/36 |

OTHER PUBLICATIONS

Patent Abstracts of Japan, vol. 014, No. 423 (C–0757), 1990 & J02160706, 1990.

Derwent Publication, Database WPI, Section Ch, Week 199603, AN 1996–026965 & Patent Abstracts of Japan, vol. 1996, No. 03, 1996 & JP 07300403, 1995.

*Primary Examiner*—Jose' G. Dees
*Assistant Examiner*—Alton Pryor

[57] ABSTRACT

This invention relates to herbicidal mixtures comprising halosulfuron-methyl and at least one compound selected from the group consisting of bensulfuron-methyl, azimsulfuron, pyrazosulfuron-ethyl, imazosulfuron, cyclosulfamuron and ethoxysulfuron, herbicidal compositions of said mixtures, and a method for the use of said mixtures to control undesired vegetation.

3 Claims, No Drawings

HERBICIDAL MIXTURES

This application claims the priority benefit of U.S. Provisional Application No. 60/094,359, filed Jul. 28, 1998.

BACKGROUND OF THE INVENTION

The control of undesired vegetation is extremely important in achieving high crop efficiency. Achievement of selective control of the growth of weeds especially in such useful crops as rice, soybeans, sugar beets, corn, potatoes, wheat, barley, tomatoes and plantation crops among others is very desirable. Unchecked weed growth in such useful crops can cause significant reduction in productivity and thereby result in increased costs to the consumers. The control of undesired vegetation in noncrop areas is also important. The need for finding products that achieve such results continues to be commercially important.

Combinations of herbicides are typically used to broaden the spectrum of plant control or enhance the level of control of any given species through additive effect. Certain rare combinations surprisingly give a greater-than-additive or synergistic effect. Such valuable combinations have now been discovered.

SUMMARY OF THE INVENTION

This invention relates to mixtures of methyl 3-chloro-5-[[[[(4,6-dimethoxy-2-pyrimidinyl)amino]carbonyl]amino]sulfonyl]-1-methyl-1H-pyrazole-4-carboxylate (halosulfuron-methyl, Formula I)

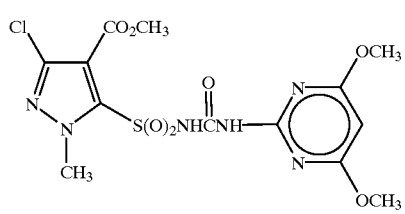

or an agriculturally suitable salt thereof with at least one sulfonylurea compound selected from the group consisting of: methyl 2-[[[[[(4,6-dimethoxy-2-pyrimidinyl)amino]carbonyl]amino]sulfonyl]methyl]benzoate (bensulfuron-methyl, IIa)

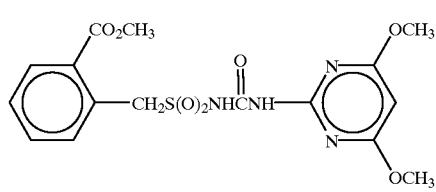

or an agriculturally suitable salt thereof,

N-[[(4,6-dimethoxy-2-pyrimidinyl)amino]carbonyl]-1-methyl-4-(2-methyl-2H-tetrazol-5-yl)-1H-pyrazole-5-sulfonamide (azimsulfuron, IIb)

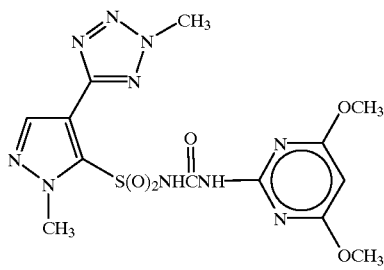

or an agriculturally suitable salt thereof, ethyl 5-[[[[(4,6-dimethoxy-2-pyrimidinyl)amino]carbonyl]amino]sulfonyl]-1-methyl-1H-pyrazole-4-carboxylate (pyrazosulfuron-ethyl, IIc)

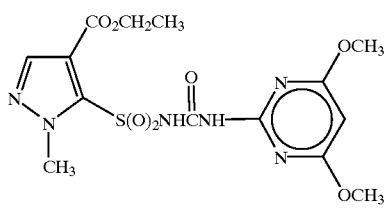

or an agriculturally suitable salt thereof, 2-chloro-N-[[(4,6-dimethoxy-2-pyrimidinyl)amino]carbonyl]imidazo[1,2-α]pyridine-3-sulfonamide (imazosulfuron, IId)

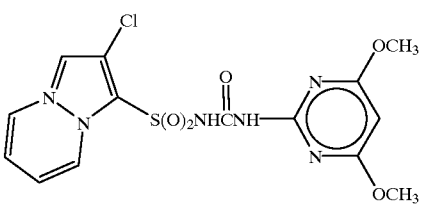

or an agriculturally suitable salt thereof,

N-[[[2-(cyclopropylcarbonyl)phenyl]amino]sulfonyl]-$N^1$-(4,6-dimethoxypyrimidin-2-yl)urea (cyclosulfamuron, IIe)

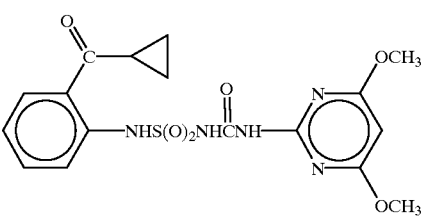

or an agriculturally suitable salt thereof, and 2-ethoxyphenyl [[(4,6-dimethoxy-2-pyrimidinyl)amino]carbonyl]sulfamate (ethoxysulfuron, IIf)

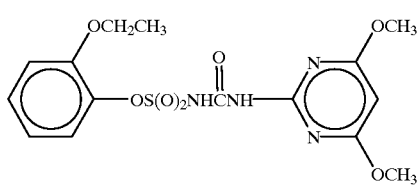

or an agriculturally suitable salt thereof, which have now been discovered to synergistically control weeds. This invention also relates to herbicidal compositions comprising herbicidally effective amounts of the aforesaid mixtures and at least one of the following: surfactant, solid or liquid diluent. This invention also relates to a method of controlling undesired vegetation comprising applying to the locus of the vegetation herbicidally effective amounts of the aforesaid mixtures.

The mixtures of the invention preferred for enhanced herbicidal utility include:

a) the compound of Formula I and the compound of Formula IIa, b) the compound of Formula I and compound of Formula IIb, c) the compound of Formula I and the compounds of Formulae IIa and IIb, d) the compound of Formula I and the compound of Formula IIc, e) the compound of Formula I and the compound of Formula IId, f) the compound of Formula I and the compound of Formula IIe, and g) the compound of Formula I and the compound of Formula IIf.

Also preferred are herbicidal compositions comprising aforesaid preferred mixtures and at least one of the following: surfactant, solid or liquid diluent. Also preferred are methods for controlling undesired vegetation comprising applying to the locus of the vegetation herbicidally effective amounts of aforesaid preferred mixtures or preferred herbicidal compositions.

Most preferred for enhanced herbicidal utility are mixtures of the invention comprising the compound of Formula I and the compound of Formula IIa, and herbicidal compositions comprising said most preferred mixtures and at least one of the following: surfactant, solid or liquid diluent. Also most preferred are methods for controlling undesired vegetation comprising applying to the locus of the vegetation herbicidally effective amounts of aforesaid most preferred mixtures or most preferred herbicidal compositions.

For reason of weed control spectrum and/or crop selectivity, the preferred application of the mixtures of this invention is in rice crops, especially in paddy rice cultivation.

DETAILS OF THE INVENTION

The Formula I compound can be prepared as described in U.S. Pat. No. 4,668,277. A synthesis involves the coupling of the pyrazolesulfonyl isocyanate of Formula 1 with the heterocyclic amine of Formula 2.

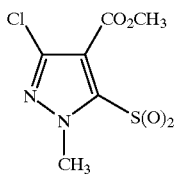

The Formula IIa compound can be prepared as described in U.S. Pat. No. 4,420,325. A synthesis involves the reaction of the benzylsulfonyl isocyanate of Formula 3 with the heterocyclic amine of Formula 2.

The Formula IIb compound can be prepared as described in U.S. Pat. No. 4,746,353. A synthesis involves the coupling of the pyrazolesulfonamide of Formula 4 with the heterocyclic carbamate of Formula 5.

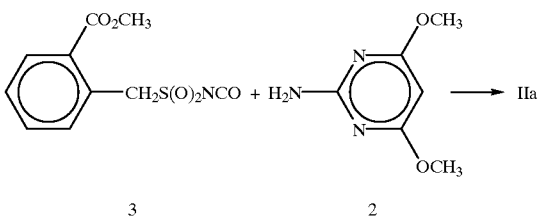

The Formula IIc compound can be prepared as described in U.S. Pat. Nos. 4,931,081 and 4,954,164. A synthesis involves the coupling of the pyrazolesulfonyl isocyanate of Formula 6 with the heterocyclic amine of Formula 2.

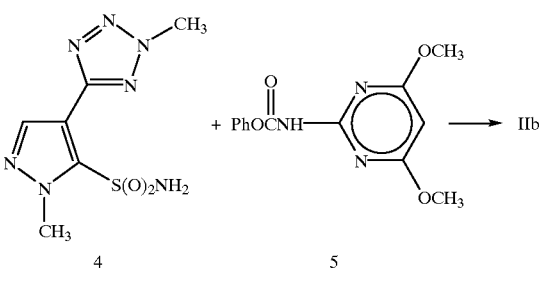

The Formula IId compound can be prepared as described in U.S. Pat. Nos. 4,994,571 and 5,017,212. A synthesis involves the coupling of the phenyl carbamate of Formula 7 with the heterocyclic amine of Formula 2 in the presence of acid.

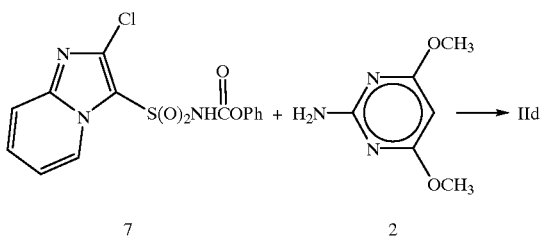

The Formula IIe compound can be prepared as described in U.S. Pat. No. 5,009,699. A synthesis involves the coupling of the aniline of Formula 8 with the sulfonyl chloride of Formula 9 in the presence of a base such as triethylamine.

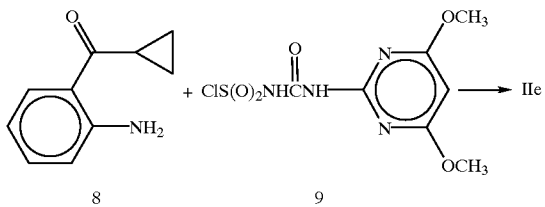

PCT publication WO 97/08151 describes salts of the Formula IIe compound.

The Formula IIf compound can be prepared as described in U.S. Pat. No. 5,104,443. A synthesis involves the coupling of the phenoxysulfonyl isocyanate of Formula 10 with the heterocyclic amine of Formula 2 in the presence of a base such as triethylamine.

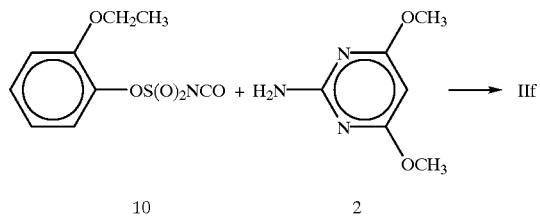

The mixtures of the present invention can include the sulfonylurea compounds of Formulae I and IIa to IIf as one or more of their agriculturally suitable salts. These can be prepared in a number of ways known in the art. For example, metal salts can be made by contacting the respective sulfonylurea compounds of Formulae I and IIa to IIf with a solution of an alkali or alkaline earth metal salt having a sufficiently basic anion (e.g., hydroxide, alkoxide, carbonate or hydride). Quaternary amine salts can be made by similar techniques.

Salts of the sulfonylurea compounds of Formulae I and IIa to IIf can also be prepared by exchange of one cation for another. Cationic exchange can be effected by direct contact of an aqueous solution of a salt of the respective sulfonylurea of Formula I or IIa to IIf (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a sulfonylurea of Formulae I or IIa to IIf (e.g., an alkali metal or quaternary amine salt) through a column packed with a cation-exchange resin containing the cation to be exchanged for that of the original salt and the desired product is eluted from the column. This method is particularly useful when the desired salt is water soluble (e.g., a potassium, sodium or calcium salt).

Formulation

The mixtures of the Formula I compound with the Formulae IIa to IIf compounds can be formulated in a number of ways:

(a) the Formula I and Formulae IIa to IIf compounds can be formulated separately and applied separately or applied simultaneously in an appropriate weight ratio, e.g., as a tank mix; or
  (b) the Formula I and Formulae IIa to IIf compounds can be formulated together in the proper weight ratio.

Mixtures of the Formula I and Formulae IIa to IIf compounds will generally be used in formulation with an agriculturally suitable carrier comprising a liquid or solid diluent and/or a surfactant wherein the formulation is consistent with the physical properties of the active ingredients, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredients can be (micro) encapsulated and further formed into a suspension or solid formulation; alternatively the entire formulation of active ingredient can be encapsulated (or "overcoated"). Encapsulation can control or delay release of the active ingredients. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, N.Y., 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfturyl alcohol.

Solutions, including emulsifiable concentrates, can be prepared by simply mixing the ingredients. Chemically stabilized aqueous sulfonylurea or agriculturally suitable sulfonylurea salt dispersions are taught in U.S. Pat. No. 4,936,900. Solution formulations of sulfonylureas with improved chemical stability are taught in U.S. Pat. No. 4,599,412. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, N.Y., 1963, pages 8–57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways.

Example A

High Strength Concentrate

| | |
|---|---|
| halosulfuron-methyl | 1.0% |
| bensulfuron-methyl | 97.5% |
| silica aerogel | 0.5% |
| synthetic amorphous fine silica | 1.0%. |

Example B

Wettable Powder

| | |
|---|---|
| halosulfuron-methyl | 59.1% |
| bensulfuron-methyl | 5.9% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| halosulfuron-methyl | 7.1% |
| bensulfuron-methyl | 2.9% |
| attapulgite granules (low volatile matter, 0.71/0.30 mm; U.S.S. No. 25–50 sieves) | 90.0%. |

Example D

Extruded Pellet

| | |
|---|---|
| halosulfuron-methyl | 3.1% |
| bensulfuron-methyl | 21.9% |
| anhydrous sodium sulfate | 10.0% |
| crude calcium ligninsulfonate | 5.0% |
| sodium alkylnaphthalenesulfonate | 1.0 |
| calcium/magnesium bentonite | 59.0%. |

Example E

High Strength Concentrate

| | |
|---|---|
| halosulfuron-methyl | 59.1% |
| azimsulfuron | 39.4% |
| silica aerogel | 0.5% |
| synthetic amorphous fine silica | 1.0%. |

Example F

High Strength Concentrate

| | |
|---|---|
| halosulfuron-methyl | 32.5% |
| bensulfuron-methyl | 55.1% |
| azimsulfuron | 10.9% |
| silica aerogel | 0.5% |
| synthetic amorphous fine silica | 1.0%. |

Example G

High Strength Concentrate

| | |
|---|---|
| halosulfuron-methyl | 32.5% |
| bensulfuron-methyl | 54.4% |
| metsulfuron-methyl | 11.6% |
| silica aerogel | 0.5% |
| synthetic amorphous fine silica | 1.0%. |

Example H

High Strength Concentrate

| | |
|---|---|
| halosulfuron-methyl | 59.1% |
| pyrazosulfuron-ethyl | 39.4% |
| silica aerogel | 0.5% |
| synthetic amorphous fine silica | 1.0%. |

Example I

High Strength Concentrate

| | |
|---|---|
| halosulfuron-methyl | 24.6% |
| imazosulfuron | 73.9% |
| silica aerogel | 0.5% |
| synthetic amorphous fine silica | 1.0%. |

Example J

High Strength Concentrate

| | |
|---|---|
| halosulfuron-methyl | 24.6% |
| cyclosulfamuron | 73.9% |
| silica aerogel | 0.5% |
| synthetic amorphous fine silica | 1.0%. |

Example K

High Strength Concentrate

| | |
|---|---|
| halosulfuron-methyl | 39.4% |
| ethoxysulfuron | 59.1% |
| silica aerogel | 0.5% |
| synthetic amorphous fine silica | 1.0%. |

Utility

Mixtures of the herbicidal compounds of Formula I and Formulae IIa to IIf are now discovered to provide unexpected synergistic control of selected weeds while retaining selective safety to certain annual monocot crops such as rice. The mixtures of the invention are effective in selectively controlling the growth of undesirable upland and aquatic grass, broadleaf, and sedge weed species while having little or no effect upon transplanted or direct seeded japonica or indica rice. The synergism these mixtures provide in controlling sedges such as yellow nuts edge (*Cyperus esculentus*) without injury to rice is both very valuable and remarkable, as sedges are particularly troublesome weeds in rice. By applying the mixtures of this invention to dry or flooded soil infested with weed seed, or application to the foliage of weed plants, or application to water covering foliage, seeds or plant parts, weeds are killed or sufficiently injured to provide the rice crop a competitive advantage. A particularly useful mode of application involves applying the mixtures of the invention to foliage of weeds before flooding the rice field or paddy.

Herbicidally effective amounts of the compounds of Formula I and Formulae IIa to IIf will vary depending on environmental conditions, formulation, method of application, amount and type of vegetation present, etc. The use ratios described hereafter refer to weights of the active ingredients. The use rate ratios of Formula I to Formula IIa are in general 10:1 to 1:100, with ratios of 5:2 to 1:7 preferred for most uses. The use rate ratios of Formula I to Formula IIb are in general 100:3 to 1:50, with ratios of 5:1 to 1:2 preferred for most uses. The use rate ratios of Formula I to Formula IIc are in general 100:3 to 1:50, with ratios of 5:1 to 1:2 preferred for most uses. The use rate ratios of Formula I to Formula IId are in general 5:1 to 1:150, with ratios of 1:1 to 1:10 preferred for most uses. The use rate ratios of Formula I to Formula IIe are in general 5:1 to 1:100, with ratios of 1:1 to 1:8 preferred for most uses. The use rate ratios of Formula I to Formula IIf are in general 10:1 to 1:100, with ratios of 3:1 to 1:6 preferred for most uses. In general, the Formula I compound (halosulfuron methyl) is applied at a rate from 1 to 100 g ai/ha, and preferably the Formula I compound is applied at a rate from 10 to 50 g ai/ha. In general, the Formula IIa compound (bensulfuron methyl) is applied at a rate from 10 to 100 g ai/ha, and preferably the Formula IIa compound is applied at a rate from 20 to 70 g ai/ha. In general, the Formula IIb compound (azimsulfuron) is applied at a rate from 3 to 50 g ai/ha, and preferably the Formula IIb compound is applied at a rate from 5 to 20 g ai/ha. In general, the Formula IIc compound (pyrazosulfuron ethyl) is applied at a rate from 3 to 50 g ai/ha, and preferably the Formula IIc compound is applied at a rate from 5 to 20 g ai/ha. In general, the Formula IId compound (imazosulfuron) is applied at a rate from 25 to 150 g ai/ha, and preferably the Formula IId compound is applied at a rate from 50 to 100 g ai/ha. In general, the Formula IIe compound (cyclosulfamuron) is applied at a rate from 25 to 100 g ai/ha, and preferably the Formula IIe compound is applied at a rate from 50 to 75 g ai/ha. In general, the Formula IIf compound (ethoxysulfuron) is applied at a rate from 5 to 100 g ai/ha, and preferably the Formula IIf compound is applied at a rate from 30 to 60 g ai/ha. One skilled in the art can readily determine application rates and ratios of the herbicide of Formula I to the herbicides of Formulae IIa to IIf as well as timing necessary for the desired level of weed control and crop safety. Synergism will be most evident at application rates at which the individual components alone do not provide complete weed control.

For practical use as herbicide treatments, the mixtures of the invention may be employed in further admixture with other known herbicides and agricultural crop protection chemicals to provide additional spectrum of activity against additional weed species. Herbicides which may be mixed include, but are not limited to, anilofos, benfuresate, benxofenap, bromobutid, cyhalofop-butyl, cafenstrole, dimepiperate, epoprodan, etobenzanid, mefenacet, metsulfuron-methyl, pretilachlor, propanil, pyributicarb, pyrazolate, thenylchlor and thiobencarb. Propanil is a particularly useful herbicide mixture partner for the mixtures of the invention.

Additionally, the mixtures of the invention may be combined with agriculturally acceptable additives such as surfactants, safeners, spreaders, emulsifiers or fertilizers, to improve performance. The mixtures of the invention will generally be used as formulated compositions.

The following Test demonstrates the control efficacy of mixtures of this invention against a specific weed. The weed control afforded by the mixtures is not limited, however, to these species. In these tests, Compound 1 is the Formula I compound, which is halosulfuron methyl, and Compound 2 is the Formula IIa compound, which is bensulfuron methyl.

BIOLOGICAL EXAMPLES OF THE INVENTION

Test A Protocol

Treatments were applied preflood as formulated products in a foliar spray to a solid stand of yellow nuts edge (*Cyperus esculentus*) that ranged in height from just emerging to about 33 cm in height, with the majority being about 23 cm in height. The experimental design was a randomized complete block with three replications. A permanent flood was established 5 days after herbicide application. The amount of weed control was determined 27 days later by visual evaluations. Plant response ratings, summarized in Table A, are based upon a 0 to 100 scale where 0 is no effect and 100 is complete control.

Colby's equation was used to calculate the expected additive herbicidal effect of the mixtures of Compound 1 with Compound 2. Colby's equation (Colby, S. R. "Calculating Synergistic and Antagonistic Responses of Herbicide Combinations," *Weeds*, 15(1), pp 20–22 (1967)) calculates the expected additive effect of herbicidal mixtures, and for two active ingredients is of the form:

$$P_{a+b}=P_a+P_b-(P_aP_b/100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

Combinations of Compound 1 with Compound 2 were surprisingly found to provide better control of yellow nuts edge than expected by calculation from Colby's equation, thus demonstrating synergism. Table A lists visual assessments of control of the weed with Compound 1 and Compound 2 applied alone as single active ingredients, applied as a mixture of the two active ingredients of Compound 1 and Compound 2, and the expected additive effect of the herbicidal mixture of Compound 1 and Compound 2 (Colby's equation). Different ratios of Compound 1 to Compound 2, and different formulation types, also provide useful weed control from the combination of the two herbicides.

TABLE A*

Effect of Compound 1 and Compound 2 as
Active Ingredients Alone and in Mixture

| Compound 1 | Compound 2 | Yellow Nutsedge Observed | Expected† |
|---|---|---|---|
| Alone | | | |
| 13.2 | 0 | 70 | — |
| 26.3 | 0 | 84 | |
| 39.5 | 0 | 88 | — |
| 0 | 21 | 15 | — |
| 0 | 42 | 23 | — |
| Mixtures | | | |
| 13.2 | 21 | 89 | 75 |
| 26.3 | 21 | 92 | 86 |
| 39.5 | 21 | 92 | 90 |
| 13.2 | 42 | 88 | 77 |
| 26.3 | 42 | 92 | 88 |
| 39.5 | 42 | 94 | 91 |

*Application rates are expressed in g ai/ha for both Compound 1 and Compound 2. Data are reported as percent control.
†Expected from the Colby Equation.

As can be seen from this test, combinations of halosulfuron methyl (Compound 1) with bensulfuron methyl (Compound 2) provided synergistic control of yellow nuts edge at all application rates tested. The synergism was greatest at the lower application rates, because at the upper application rates the expected control was approaching 100% and thus little enhancement of activity was possible. The surprising synergism discovered results in obtaining excellent control of yellow nuts edge at application rates that would be expected to provide only moderate control. This enhanced control of such troublesome weeds makes the mixtures of the invention particularly useful and valuable.

What is claimed is:

1. A synergistic herbicidally effective mixture of halosulfuron-methyl (Formula I)

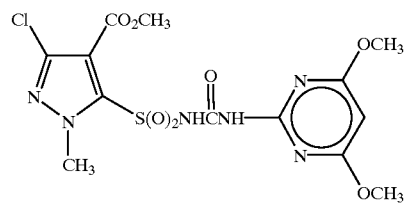

or an agriculturally suitable salt thereof with bensulfuron-methyl (Formula IIa),

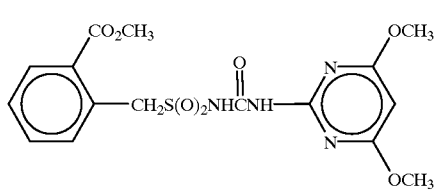

or an agriculturally suitable salt thereof.

2. An agriculturally suitable composition for controlling the growth of undesired vegetation comprising an effective amount of the mixture of claim 1 and at least one of the following: surfactant, solid or liquid diluent.

3. A method for controlling the growth of undesired vegetation by applying to the locus of the undesired vegetation a herbicidally effective amount of the mixture of claim 1.

* * * * *